United States Patent [19]

Grover et al.

[11] Patent Number: 4,931,460

[45] Date of Patent: Jun. 5, 1990

[54] POST-ISCHEMIC MYOCARDIAL DYSFUNCTION USING THROMBOXANE $A_2$ ANTAGONISTS

[75] Inventors: Gary J. Grover, Stockton, N.J.; Irvin E. Fulmor, III, Wrightstown, Pa.

[73] Assignee: E. R. Squibb & Sons, Inc., Princeton, N.J.

[21] Appl. No.: 98,424

[22] Filed: Sep. 17, 1987

[51] Int. Cl.$^5$ .................. A61K 31/34; A61K 31/357; G07D 307/00

[52] U.S. Cl. .................................... 514/381; 514/456

[58] Field of Search ................ 514/456, 381; 549/463

[56] References Cited

U.S. PATENT DOCUMENTS

| | | | |
|---|---|---|---|
| 4,416,896 | 11/1983 | Nakane et al. | 424/285 |
| 4,663,336 | 5/1987 | Nakane et al. | 514/381 |

OTHER PUBLICATIONS

Schror, K. et al., "Treatment of Acute Myocardial Ischemia with a Selective Antagonist of Thromboxane Receptors", *Br. J. Pharmacol.*, 1986, 87:631-7.

Ogletree, M. L. et al., "Pharmacological Actions of SQ 29,548 a Novel Thromboxane Antagonist", *J. Pharmacol. Ex. Ther.*, 1985; 234:435-41.

Hoeft, A. et al., "Preservation of Myocardium in Transient Ischemia by the Thromboxane Synthetase Inhibitor," UK-38,485, *Res. Exp. Med.*, 1986; 186:35-46.

Schmitz, J. M. et al., "Vascular Prostaglandin and Thromboxane Production in a Canine Model of Myocardial Ischemia," *Circ. Res.*, 1985, 57:223-31.

Michael, L. H. et al., "Myocardial Ischemia: Platelet and Thromboxane Concentrations in Cardiac Lymph and the Effects of Ibuprofen and Prostacyclin," *Cir. Res.*, 1986; 59:49-55.

Grover, G. J. et al., "Effect of the Thromboxane Receptor Antagonist SQ 29,548 on Infarct Size in Dogs," *Circulation*, 1986; 74 (Suppl II): 348 (Abstract).

Pagani, M. et al., "Initial Myocardial Adjustments to Brief Periods of Ischemia and Reperfusion in the Conscious Dogs," *Circ. Res.*, 1978; 43:83-92.

*Primary Examiner*—Paul Lieberman
*Assistant Examiner*—John F. McNally
*Attorney, Agent, or Firm*—Burton Rodney

[57] ABSTRACT

A method is provided for improving post-ischemic myocardial dysfunction such as contractile dysfunction or reperfusion injury by administering a thromboxane $A_2$ antagonist before, during or immediately after an ischemic attack.

17 Claims, 2 Drawing Sheets

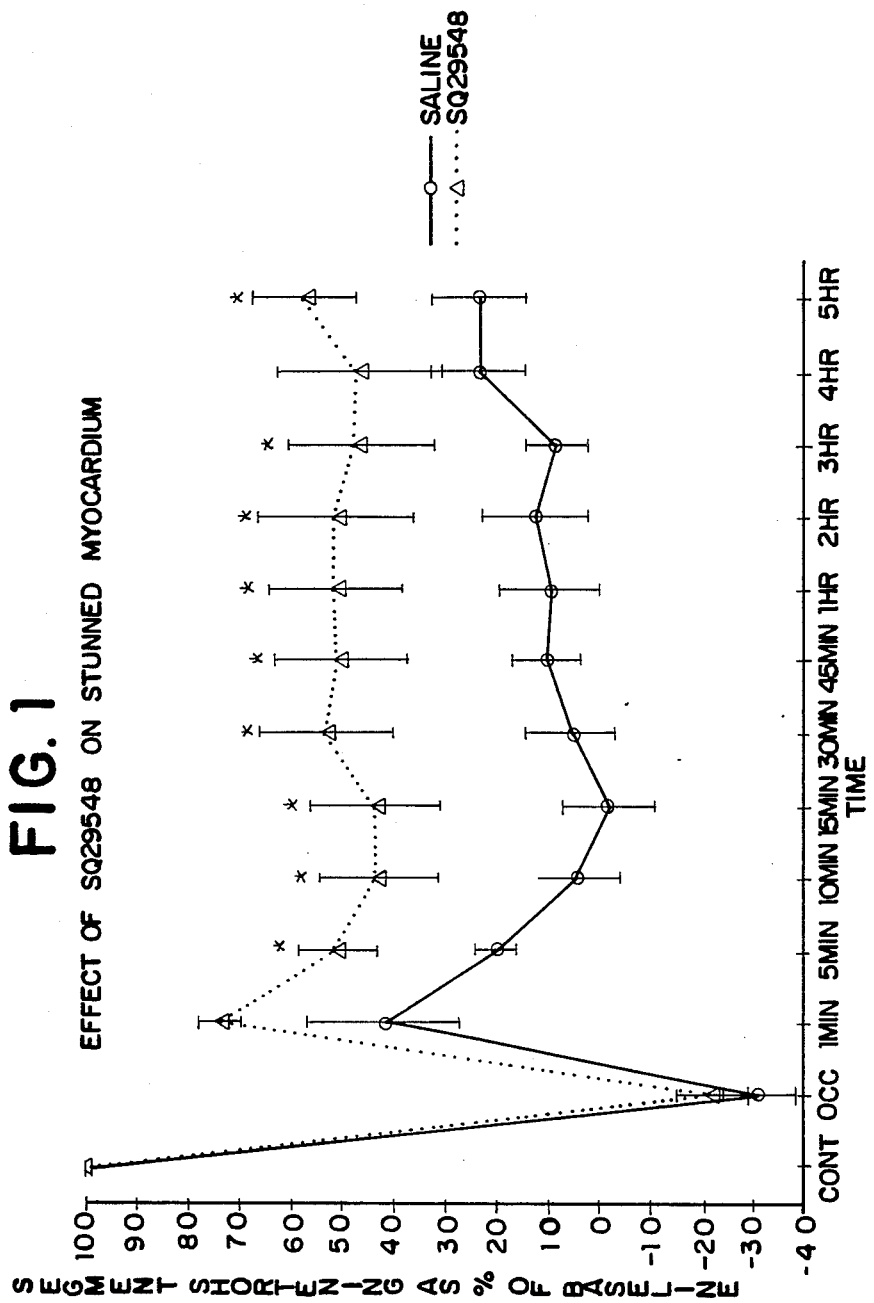

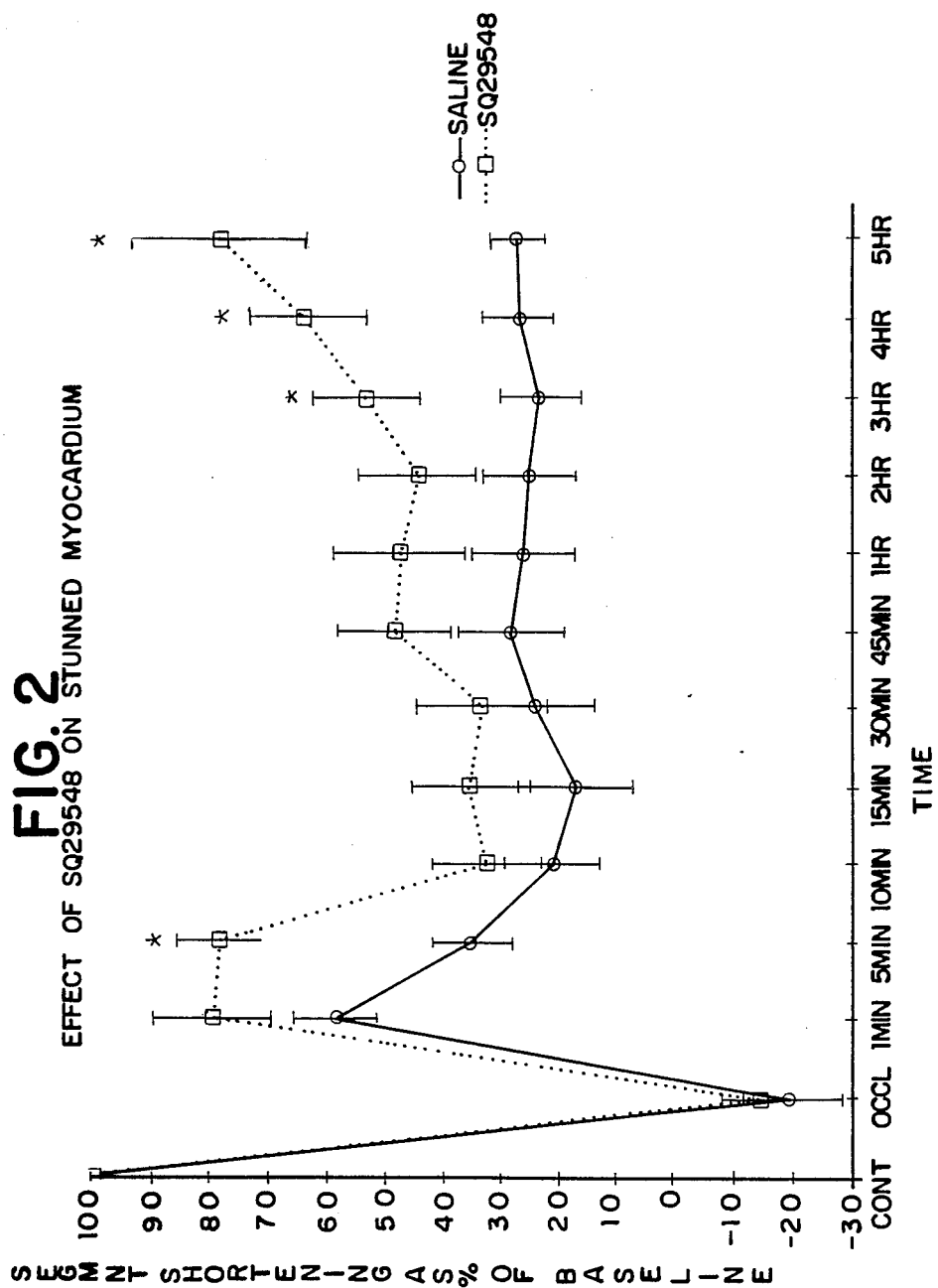

POST-ISCHEMIC MYOCARDIAL DYSFUNCTION USING THROMBOXANE A₂ ANTAGONISTS

FIELD OF THE INVENTION

The present invention relates to a method for improving post-ischemic myocardial dysfunction in mammalian species by administering a thromboxane $A_2$ antagonist to enhance the recovery of heart function.

BACKGROUND OF THE INVENTION

Blood flow reductions in the heart can result in dysfunction of this organ and cell death if the flow reduction is severe enough. Restoration of coronary blood flow early during a heart attack is becoming a clinical reality with the advent and improvements in thrombolytic, mechanical, and surgical interventions. While early restoration of blood flow, for example, by thrombolysis or following transient ischemia, can prevent or mitigate the degree of cell death (infarction) occurring, reperfusion can still result in some degree of cardiac dysfunction or cell death (also referred to as stunned myocardia). Thus, it would be of great clinical value to find a means to preserve reperfusion function of the heart.

Thromboxane $A_2$ (TXA) which is released from the heart during reperfusion is thought to have physiological effects that may adversely influence myocardial performance, namely, TXA contributes to post ischemic contractile dysfunction, Hoeft, A., et al., "Preservation of myocardium in transient ischemia by the thromboxane synthetase inhibitor." UK-38,485. *Res. Exp. Med.* 1986; 186:35–46, and Schror, K., et al. "Treatment of acute myocardial ischemia with a selective antagonist of thromboxane receptors. (BM 13,177)" *Br. J. Pharmacol.* 1986; 87:631-7.

Hoeft et al, supra, and Schror et al, supra, demonstrate the ability of TXA inhibitors or antagonists to reduce the severity of ischemia in some experimental models, though the physiological mechanisms of action of these compounds on post-ischemic recovery of function are still unknown. For instance, it is thought that TXA is released during ischemia as well as during reperfusion and thus TXA antagonists may be working during coronary occlusion Schmitz, J. M., et al., "Vascular prostaglandin and thromboxane production in a canine model of myocardial ischemia." *Circ. Res.* 1985 57:223-31, Michael, L. H., et al., "Myocardial ischemia: platelet and thromboxane concentrations in cardiac lymph and the effects of ibuprofen and prostacyclin." *Circ. Res.* 1986; 59:49-55.

DESCRIPTION OF THE INVENTION

In accordance with the present invention, a method is provided for treating post-ischemic myocardial dysfunction in mammalian species to improve heart function, wherein a therapeutically effective amount of a thromboxane $A_2$ antagonist is systemically administered, such as orally or parenterally, or by catheter, prior to, during or after reperfusion to mitigate the post-ischemic adverse effects of thromboxane on heart function during periods of myocardial occlusion and reperfusion.

The term "reperfusion" is employed herein to refer to release of occlusion and resumption of blood flow.

It has been found that the thromboxane $A_2$ antagonist improves post-ischemic performance of the heart by improving post-ischemic contractile function when administered during both the coronary occlusion period and the reperfusion period or only during the reperfusion period. Such improvement in post-ischemic performance of the heart is evidenced by decreased contractile dysfunction and decrease in tissue necrosis.

Thromboxane $A_2$ antagonists which may be employed herein include the 7-oxabicycloheptane and 7-oxabicycloheptene compounds disclosed in U.S. Pat. No. 4,537,981 to Snitman et al, especially, [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid; the 7-oxabicycloheptane substituted aminoprostaglandin analogs disclosed in U.S. Pat. No. 4,416,896 to Nakane et al., especially, [1S-[1α,2β(5Z),3β,4α]]-7-[3=[[2-(phenylamino)carbonyl]-hydrazino]methyl]7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1β,2=(5Z), 3α,4β]]-7-[3-[[[[(1-oxoheptyl)amino]acetyl]amino]methyl]-7-oxabicyclo[2.2.1]hept-2-yl]-5-heptenoic acid and the corresponding tetrazole, and [1S-[1<α,2<β(Z)-,3<β,4<α]]-7-[3-[[[[(4-cyclohexyl-1-oxobutyl-)amino]acetyl]amino]methyl]-7-oxabicyclo[2.2.1]hept-2-yl]-5-heptenoic acid; the phenoxyalkyl carboxylic acids disclosed in U.S. Pat. No. 4,258,058 to Witte et al, especially 4-[2-(benzenesulfamido)ethyl]phenoxyacetic acid, (BM 13,177—Boehringer Mannheim), the sulphonamidophenyl carboxylic acids disclosed in U.S. Pat. No. 4,443,477 to Witte et al, especially 4-[2-(4-chlorobenzenesulfonamido)ethyl]phenylacetic acid, (BM 13,505, Boehringer Mannheim) the arylthioalkylphenyl carboxylic acids disclosed in U.S. application Ser. No. 067,199 filed June 29, 1987, especially 4-(3-((4-chlorophenyl)sulfonyl)propyl)benzeneacetic acid.

Other examples of thromboxane $A_2$ inhibitors suitable for use herein include, but are not limited to (E)-5-[[[(pyridinyl)[3-(trifluoromethyl)phenyl]methylene]amino]oxy]pentanoic acid also referred to as R68,070—Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, 17 Mar. 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol 90 (Proc. Suppl):228 P-Abs., March 87), 5(E)-7-[2,2-dimethyl-4-phenyl-1,3-dioxan-cis-5-yl]heptenoic acid (ICI 159995, Brit. J. Pharmacol. 86 (Proc. Suppl):808 P-Abs., Dec. 85), N,N'-bis[7-(3-chlorobenzeneaminosulfonyl)-1,2,3,4-tetrahydro-isoquinolyl]-disulfonylimide (SKF 88046, Pharmacologist 25(3):116 Abs, 117 Abs, August 83), [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848—Glaxo, Circulation 72(6):1208, December 85, levallorphan allyl bromide (CM 32,191, Sanofi, Life Sci. 31 (20-21):2261, 15 November 82), (Z,2-endo-3-oxo)-7-(3-acetyl-2-bicyclo[2.2.1]heptyl-5-hepta-3Z-enoic acid, 4-phenylthiosemicarbazone (EP092 —Univ. Edinburgh, Brit, J. Pharmacol. 84(3):595, March 85).

The disclosure of the above-mentioned patents, patent applications and other references are incorporated herein by reference.

In carrying out the method of the present invention, the thromboxane $A_2$ antagonist may be administered to mammalian species, such as monkeys, dogs, cats, rats, humans, etc. during the period of coronary occlusion and/or during the period of reperfusion and/or shortly after termination of the ischemic attack, for example within 1 to 2 hours after the ischemia.

Although the thromboxane $A_2$ antagonist may be administered systemically, such as orally or parenterally, it is preferred that the thromboxane $A_2$ antagonist be administered locally to the coronary arteries by catheter such as by arterial angiography or intracoronary injection.

With regard to dosage of thromboxane $A_2$ antagonist, where the drug is administered by arterial angiography or intracoronary injection, from about 0.1 to about 30 mg/kg/treatment and preferably from about 0.5 to about 25 mg/kg/treatment will be employed. The number of treatments will depend upon the length of the ischemic attack and the progress of reperfusion to achieve normal heart function. Usually, from 1 to 5 treatments per day will be required for as long as contractile dysfunction continues.

Where the thromboxane $A_2$ antagonist is to be administered by angiography or intracoronary injection, it will be formulated in a conventional vehicle, such as distilled water, saline, Ringer's solution, or other conventional carriers.

The thromboxane $A_2$ antagonist may also be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

With regard to such systemic formulations, single or divided doses of from about 5 to about 2500 mg, preferably from about 10 to 2000 mg/one to four times daily, may be administered in systemic dosage forms as described above for a period sufficient to restore normal heart function.

REFERENCE TO ACCOMPANYING FIGURES

FIG. 1 is a graph of the effect of iv thromboxane $A_2$ antagonist (SQ 29,548) on myocardial stunning; and FIG. 2 is a graph of the effect of thromboxane $A_2$ antagonist (SQ 29,548) given 1 minute before reperfusion on stunned myocardium.

The following Examples represent preferred embodiments of the present invention.

EXAMPLE 1

An injectable solution for use in administering thromboxane $A_2$ antagonist by intracoronary injection, by arterial angiography or intravenously is produced as follows:

| | |
|---|---|
| [1S-[1α,2β(5Z),3β,4α]]-7-[3-[[2-(phenylamino)carbonyl]hydrazino]-methyl]-7-oxabicycol[2.2.1]hept-2-yl]-5-heptenoic acid (SQ 29,548) | 2500 mg |
| Methyl paraben | 5 mg |
| Propyl paraben | 1 mg |
| Sodium chloride | 25 g |
| Water for injection qs. | 5 l. |

The thromboxane $A_2$ antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in improving post-ischemic contractile dysfunction is prepared as described in Example 1 except that the thromboxane $A_2$ antagonist employed is the phenoxyalkyl carboxylic acid 4-[2-(benzenesulfamido)ethyl]phenoxyacetic acid, disclosed in U.S. Pat. No. 4,258,058.

EXAMPLE 3

An injectable solution for use in administering thromboxane $A_2$ antagonist by intracoronary injection, by arterial angiography or intravenously containing [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid (SQ 30,741) as the thromboxane $A_2$ antagonist is prepared as described in Example 1.

EXAMPLE 4

An injectable for use in improving post-ischemic contractile dysfunction is prepared as described in Example 1 except that the thromboxane $A_2$ antagonist employed is [1S-[1<α,2<β(Z),3<β,4<α]]-7-[3-[[[[(4-cyclohexyl-1-oxobutyl)amino]acetyl]amino]methyl]-7-oxabicyclo[2.2.1]hept-2-yl]-5-heptenoic acid.

EXAMPLE 5

A thromboxane $A_2$ antagonist formulation suitable for oral administration is set out below.

1000 tablets each containing 400 mg of thromboxane $A_2$ antagonist were produced from the following ingredients.

| | |
|---|---|
| [1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid (SQ 30,741) | 400 mg |
| Corn starch | 50 g |
| Gelatin | 7.5 g |
| Avicel (microcrystalline cellulose) | 25 g |
| Magnesium stearate | 2.5 g |

The thromboxane antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLE 6

The following experiment was conducted to determine the effect of the TXA antagonist, [1S-[1α,2β(5Z),3β,4α]]-7-[3-[[2-(phenylamino)carbonyl]hydrazino]methyl]-7-oxabicyclo[2.2.1]- hept-2-yl]-5-heptenoic acid (also referred to as SQ 29,548), on post-ischemic contractile function during (1) the coronary occlusion and reperfusion periods and (2) during reperfusion alone.

Methods

Adult mongrel dogs (10–15 mg) were anesthetized using pentobarbital sodium (30 mg/kg, i.v.). Aortic blood pressure was measured using a Mikro-tip catheter transducer (Millar Instruments) inserted into the right carotid artery. The right femoral artery was catheterized for collection of blood for measurement of blood gases. A left femoral venous catheter was inserted for drug infusion and supplemental anesthesia.

Each animal was intubated and placed on artificial respiration such that eucapnia was maintained. They were then subjected to a left thoracotomy and the pericardium was formed into a cradle. The left anterior descending coronary artery (LAD) was isolated proximal to its first branch and a silk ligature was placed around it. In animals to be given intracoronary (i.c.) injections, a bent 27 gauge needle with an attached catheter was inserted into the LAD distal to the ligature. A left atrial catheter was implanted for injection of dye (determination of area at risk at the end of the experiment). Segmental shortening in the LAD perfused region was determined using ultrasonic piezoelectric crystals implanted into the subendocardium of this region. The crystals in each pair were placed approximately 10 mm apart.

At this time, the animals were divided into 4 groups: 1. Animals given i.v. saline (n=9) starting 15 min before LAD occlusion. 2. Animals given the TXA antagonist SQ 29,548 (0.20 mg/kg+0.20 mg/kg/hr, n=7) i.v. starting 15 minutes before LAD occlusion. 3. Animals given i.c. SQ 29,548 (0.20 mg/kg+0.2 mg/kg/hr, n=7) starting 1 minute before reperfusion. 4. Animals given i.c. saline starting 1 minute before reperfusion (n=11). The subject TXA antagonist is a potent and selective TXA/prostaglandin endoperoxide antagonist (SQ 29,548) as previously described by Ogletree, M. L., et. al., "Pharmacological actions of SQ 29,548, a novel selective thromboxane antagonist," *J. Pharmacol. Exp. Ther.* 1985; 234:435–41. The dose of the TXA antagonist used has been shown to be effective in blocking >99% of TXA receptors, Grover, G. J., et al., "Effect of the thromboxane receptor antagonist SQ 29,548 on infarct size in dogs." *Circulation* 1986; 74 (Suppl II): 348 (Abstract). The LAD was occluded via the silk ligature for 15 minutes at which time the occlusion was released and reperfusion instituted for 5 hours. Hemodynamic and segment shortening data were collected before occlusion, during occlusion, and throughout the reperfusion period. At the end of the experiment, the area at risk was determined, by injection of patent blue violet dye into the left atrial catheter while the LAD was being perfused with Ringer's lactate at the animals' existing blood pressure. The hearts were then removed and the area at risk was then determined by tracing the hearts on transparencies and calculating the areas of interest using planimetry.

The segment shortening data were normalized as previously described by Theroux, P., et al., "Regional myocardial function in the conscious dog during acute coronary occlusion and responses to morphine, propranolol, nitroglycerin and lidocaine." *Circulation* 1976; 53:302–14. Shimshak, T. M., et al. "Recovery of contractile function in post-ischemic reperfused myocardium of conscious dogs: influence of nicorandil, a new antianginal agent." *Cardiovasc. Res.* 1986; 20:621–6. End diastolic length (EDL) as well as end systolic length (ESL) were determined and the percentage segment shortening (% SS) was calculated from the equation: % SS=(EDL−ESL)/EDL.

All data are presented as mean ±SE. Between treatment hemodynamic comparisons were made using a one-way analysis of variance and multiple comparisons were determined using the Newman-Keuls test. Segment shortening was expressed as a percent of initial baseline values and between treatment comparisons were made using the Kruskal-Wallis test for nonparametric data. A value of $p<0.05$ was accepted as significant.

Results

Hemodynamic data for i.v. saline- and TXA antagonist (SQ 29,458)-treated animals are shown on Table 1. Arterial blood pressure and heart rate were similar under baseline conditions for both groups shown on this table and did not change during the experiment. Arterial blood gases were maintained within the normal range for dogs throughout the experiment.

The effect of i.v. SQ 29,548 (0.20 mg/kg +0.20 mg/kg/hr, n=7) pretreatment (given 15 minutes before LAD occlusion) on segmental shortening during occlusion and reperfusion is shown on FIG. 1. The segmental shortening in the LAD region is expressed as a percent of baseline, pre-treatment (pre-occlusion) values in this figure. Occlusion of the LAD resulted in a marked systolic bulging in both groups. This occlusion value was measured 1 minute before reperfusion. Upon reperfusion, segmental shortening immediately returned towards baseline values in both drug- and saline-treated animals. At 5–15 minutes, function was again markedly reduced such that in saline-treated animals, segmental shortening was nearly nonexistent. In animals treated with SQ 29,548, contractile function was significantly improved compared with saline-treated animals starting at 5 minute post-reperfusion. This improved function was observed at most of the reperfusion times measured. At 5 hours post-reperfusion, shortening returned to 25% of baseline values in saline-treated animals, but returned to approximately 60% in drug-treated animals. While not shown on FIG. 1, segmental shortening was measured during drug or saline treatment immediately before LAD occlusion and found that neither drug nor saline treatment had any effect on segmental shortening. The area at risk as a percent of the left ventricle was found to be nearly identical in both saline- and SQ 29,548-treated groups (30±2% and 30±8%, respectively). The crystals were always found to be in the center of the area at risk.

As seen, FIG. 1 shows use of SQ 29,548 resulted in significant (p, <0.05) improvements in reperfusion function. The hemodynamic data for animals treated with i.c. saline or SQ 29,548 just before reperfusion are shown on Table 2. Baseline pressure and heart rate values were similar for both groups and did not change throughout the experiment. Arterial blood gases were maintained within the normal range for dogs throughout the experiment.

Segmental shortening data (expressed as a % of the baseline values) for i.c. saline- and SQ 29,548-treated animals (0.20 mg/kg+0.20 mg/kg/hr, n=7 given 1 minute before reperfusion) are shown in FIG. 2. LAD occlusion again resulted in marked systolic bulging in both groups when measured 1 minute before reperfusion (immediately before drug or saline infusion). Upon reperfusion, shortening immediately returned towards baseline values in both groups. By 5 minutes post-reperfusion, function in saline-treated animals began to decrease again until at 15 minute post-reperfusion, segmental shortening was approximately 15% of baseline values. Function was better maintained in SQ 29,548-treated animals up until 10 minutes post-reperfusion at which time function dropped off markedly to values that were only slightly and nonsignificantly higher than the respective saline values. This trend continued until 3 hours post-reperfusion when segmental shortening in the LAD region began to rapidly improve in SQ 29,548-treated animals compared with saline values. This trend continued up to the end of the experiment where shortening in the affected region returned to approximately 70% of baseline values. At this time, function had returned to approximately 20% of baseline in saline-treated animals. The area at risk as a percent of the left ventricle was found to be similar in both i.c. saline- and SQ 29,548-treated groups (30±7% and 29±2% respectively). The crystals were always found to be in the center of the area at risk.

As seen in FIG. 2, with the above dosing regime, use of SQ 29,548 resulted in significant improvements (*, $p<0.05$) in reperfusion at several of the time points measured.

Discussion

Brief coronary occlusions of insufficient severity to result in tissue necrosis can still, upon reperfusion, result in significant contractile dysfunction lasting for hours or days (myocardial stunning), Pagani, M., et al., "Initial myocardial adjustments to brief periods of ischemia and reperfusion in the conscious dog," *Circ. Res.* 1978; 43:83–92; Weiner, J. M., et al. "Persistence of myocardial injury following brief periods of coronary occlusion.", *Cardiovasc. Res.* 1976; 10:678–86. The exact mechanism for this hypokinesia is still vague, though some aspects of reperfusion injury may play a deleterious role.

In the present study, the role of TXA release on myocardial stunning was determined by using a selective TXA receptor antagonist, SQ 29,548. The dose of SQ 29,548 used in this study has been found to block >99% of the TXA receptors as measured by inhibition of the renal and mesenteric arterial constrictor response to the TXA mimetic U-46619, Grover et al supra.

The model of stunned myocardium used in the present study has been used extensively before and has been found to result in a reproducible post-ischemic dysfunction, Heyndrickx, G. R., et al., "Regional myocardial functional and electrophysiological alterations after brief coronary artery occlusion in conscious dogs," *J. Clin. Invest.* 1975; 56:978–85; Heyndrickx, G. R., et al "Depression of regional blood flow and wall thickening after brief coronary occlusion," *Am. J. Physiol* 1978; 234:H653–9. As previously shown, occlusion of the LAD in the present study resulted in passive bulging during systole in all groups to a similar degree. Immediately upon reperfusion, contractile function markedly increased in saline-treated animals, but just as quickly decreased again. Function in the affected region then slowly improved, but never returned to baseline values in the 5 hours reperfusion period that was followed in this study.

Treatment with SQ 29,548 resulted in a significant improvement in post-ischemic contractile function. Pretreatment with the drug caused an improved function at most reperfusion times measured (though this study alone does not tell if the SQ 29,548 is working during the occlusion or reperfusion times). Previous studies have indicated that antagonism of TXA seems to afford a direct cardioprotective effect during occlusion, Schror et al, supra, but it was still of interest to determine if SQ 29,548 could have some or all of its protective effects during reperfusion period. When infused 1 minute before reperfusion, some improvement in function particularly during the later times measured was observed. It appears that some of the beneficial effects of SQ 29,548 on recovery of function occur during the reperfusion period, but this improvement was not as marked as that seen with pre-treatment. This indicates that SQ 29,548 can exert salutory effects during the occlusion and reperfusion periods.

Summary

Selective TXA receptor antagonists appear to improve the post-ischemic performance of the heart. This was tested using the TXA antagonist, SQ 29,548, in a model of ischemia and subsequent reperfusion. The return of function during reperfusion in these hearts was measured and it was found that SQ 29,548 markedly enhanced the recovery of heart function when given during both the coronary occlusion and reperfusion periods and when given only during the reperfusion period.

TABLE 1

| The Effect of SQ 29,548 on Hemodynamic Variables During LAD Occlusion and Reperfusion | | | | | | | | |
|---|---|---|---|---|---|---|---|---|
| | | | LAD Occlusion (14 min | Time Post Reperfusion | | | | |
| | Pre-Drug | Post-Drug | post-occlusion) | 1' | 10' | 30' | 1 hr. | 5 hr. |
| Systolic Blood Pressure (mm Hg) | | | | | | | | |
| Saline (n = 9) | 118 ± 6 | 113 ± 6 | 113 ± 6 | 109 ± 6 | 113 ± 4 | 120 ± 4 | 120 ± 4 | 123 ± 4 |
| SQ 29,548 (n = 7) | 109 ± 5 | 108 ± 5 | 106 ± 6 | 106 ± 6 | 105 ± 5 | 107 ± 5 | 111 ± 5 | 109 ± 6 |
| Diastolic Blood Pressure (mm Hg) | | | | | | | | |
| Saline (n = 9) | 92 ± 5 | 94 ± 5 | 89 ± 5 | 85 ± 6 | 84 ± 3 | 88 ± 4 | 91 ± 3 | 92 ± 3 |
| SQ 29,548 (n = 7) | 88 ± 4 | 86 ± 4 | 83 ± 5 | 82 ± 4 | 83 ± 4 | 83 ± 4 | 86 ± 4 | 80 ± 4 |
| Heart Rate (beats/min) | | | | | | | | |
| Saline (n = 9) | 157 ± 5 | 156 ± 5 | 157 ± 4 | 148 ± 5 | 155 ± 3 | 158 ± 4 | 158 ± 4 | 159 ± 3 |
| SQ 29,548 (n = 7) | 155 ± 7 | 154 ± 6 | 157 ± 7 | 152 ± 7 | 156 ± 6 | 156 ± 6 | 157 ± 5 | 161 ± 6 |

All values are mean ± SE

TABLE 2

The Effect of Saline or SQ 29,548 Given Only During Reperfusion on Hemodynamic Variables During LAD Occlusion and Reperfusion

| | Pre-Occlusion | LAD Occlusion (14 min post-occlusion) | Reperfusion | | | | |
|---|---|---|---|---|---|---|---|
| | | | 1' | 10' | 30' | 1 hr. | 5 hr. |
| Systolic Blood Pressure (mm Hg) | | | | | | | |
| Saline (n = 11) | 116 ± 6 | 118 ± 6 | 109 ± 6 | 109 ± 3 | 113 ± 4 | 116 ± 4 | 120 ± 4 |
| SQ 29,548 (n = 7) | 111 ± 3 | 107 ± 4 | 110 ± 3 | 109 ± 3 | 108 ± 3 | 112 ± 3 | 113 ± 3 |
| Diastolic Blood Pressure (mm Hg) | | | | | | | |
| Saline (n = 11) | 92 ± 6 | 94 ± 5 | 85 ± 6 | 84 ± 3 | 88 ± 3 | 89 ± 3 | 92 ± 3 |
| SQ 29,548 (n = 7) | 90 ± 3 | 85 ± 4 | 86 ± 3 | 85 ± 4 | 85 ± 3 | 88 ± 3 | 88 ± 3 |
| Heart Rate (beats/min) | | | | | | | |
| Saline (n = 11) | 146 ± 5 | 146 ± 5 | 144 ± 6 | 142 ± 6 | 145 ± 6 | 151 ± 6 | 160 ± 5 |
| SQ 29,548 (n = 7) | 138 ± 5 | 139 ± 6 | 136 ± 6 | 136 ± 6 | 136 ± 6 | 139 ± 6 | 156 ± 3 |

All values are mean ± SE

What is claimed is:

1. A method of reducing or eliminating reperfusion injury due to post-ischemic myocardial dysfunction in a mammalian species, which comprises administering to a mammalian species in need of such treatment an effective amount of a thromboxane A$_2$ antagonist to reduce or eliminate reperfusion injury and decrease contractile dysfunction and decrease tissue necrosis.

2. The method as defined in claim 1 wherein the thromboxane A$_2$ antagonist is administered by arterial angiography or by intracoronary injection, intravenously or orally.

3. The method as defined in claim 1 wherein the thromboxane A$_2$ antagonist is administered prior to during or after reperfusion.

4. The method as defined in claim 1 wherein the thromboxane A$_2$ antagonist is administered during coronary occlusion and reperfusion.

5. The method as defined in claim 1 wherein the thromboxane A$_2$ antagonist is administered only during reperfusion.

6. The method as defined in claim 1 wherein the thromboxane A$_2$ antagonist is a 7-oxabicycloheptane or a 7-oxabicycloheptene.

7. The method as defined in claim 1 wherein in thromboxane A$_2$ antagonist is a 7-oxabicycloheptane substituted amino-prostaglandin analog.

8. The method as defined in claim 1 wherein the thromboxane A$_2$ antagonist is a 7-oxabicycloheptane substituted diamide prostaglandin analog.

9. The method as defined in claim 1 wherein the thromboxane A$_2$ antagonist is a phenoxyalkyl carboxylic acid.

10. The method as defined in claim 1 wherein the thromboxane A$_2$ antagonist is a sulfonamidophenyl carboxylic acid.

11. The method as defined in claim 1 wherein the thromboxane A$_2$ antagonist is an arylthioalkylphenyl carboxylic acid.

12. The method as defined in claim 1 wherein the thromboxane A$_2$ antagonist is [1S-[1α,2β(5Z),3β(-1E,3R,4S),4α]]-7-[3-(3-hydroxy-4-phenyl-1-pentenyl)-7-oxabicyclo[2.2.1]hept-2-yl]-5-heptenoic acid.

13. The method as defined in claim 1 wherein the thromboxane A$_2$ antagonist has the name [1S-[1β,2α(5Z),3α,4β]]-7-[3-[[[[(l-oxoheptyl)amino]acetyl]amino]methyl]-7-oxabicyclo[2.2.1]-hept-2-yl]-5-heptenoic acid or the corresponding tetrazole.

14. The method as defined in claim 1 wherein the thromboxane A$_2$ antagonist has the name [1S-[1<α,-2<β(Z),3<β,4<α]]-7-[3-[[[[(4-cyclohexyl-1-oxobutyl-)amino]acetyl]amino]methyl]-7-oxabicyclo[2.2.1]hept-2-yl]-5-heptenoic acid.

15. The method as defined in claim 1 wherein the thromboxane A$_2$ antagonist has the name [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid.

16. The method as defined in claim 1 wherein the thromboxane A$_2$ antagonist has the name 4-(3-((4-chlorophenyl)sulfonyl)propyl)benzene acetic acid.

17. The method as defined in claim 1 wherein the thromboxane A$_2$ antagonist has the name or 4-[2-(benzenesulfamido)ethyl]phenoxyacetic acid or 4-[2-(4-chlorobenzenesulfonamido)ethyl]phenylacetic acid.

* * * * *